United States Patent
Janku

(10) Patent No.: US 11,141,421 B2
(45) Date of Patent: Oct. 12, 2021

(54) ANTITUMOR AGENT FOR BILIARY TRACT CANCER AND METHOD FOR TREATING BILIARY TRACT CANCER

(71) Applicant: FUJIFILM Corporation, Tokyo (JP)

(72) Inventor: Filip Janku, Houston, TX (US)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/941,674

(22) Filed: Jul. 29, 2020

(65) Prior Publication Data

US 2020/0352973 A1 Nov. 12, 2020

Related U.S. Application Data

(63) Continuation of application No. PCT/JP2018/007772, filed on Mar. 1, 2018.

(60) Provisional application No. 62/623,262, filed on Jan. 29, 2018.

(51) Int. Cl.
A61K 31/7068 (2006.01)
A61P 35/00 (2006.01)
A61K 9/00 (2006.01)

(52) U.S. Cl.
CPC ........ *A61K 31/7068* (2013.01); *A61K 9/0019* (2013.01); *A61P 35/00* (2018.01)

(58) Field of Classification Search
CPC .... A61K 31/7068; A61K 9/0019; A61P 35/00
See application file for complete search history.

(56) References Cited

U.S. PATENT DOCUMENTS

| | | | |
|---|---|---|---|
| 3,116,282 A | 12/1963 | Hunter | |
| 3,243,425 A | 3/1966 | Whistler | |
| 4,211,773 A | 7/1980 | Lopez et al. | |
| 4,220,774 A | 9/1980 | Kuehne | |
| 4,803,272 A | 2/1989 | Anton et al. | |
| 5,811,408 A | 9/1998 | Yoshimura et al. | |
| 6,103,707 A | 8/2000 | Yamada et al. | |
| 6,147,058 A | 11/2000 | Yoshimura et al. | |
| 6,448,415 B1 | 9/2002 | Lee et al. | |
| 7,148,223 B2 | 12/2006 | Secrist, III et al. | |
| 7,285,572 B2 | 10/2007 | Shinagawa et al. | |
| 7,858,788 B2 | 12/2010 | Yoshida et al. | |
| 8,329,925 B2 | 12/2012 | Voigtlander et al. | |
| 8,420,831 B2 | 4/2013 | Voigtlander et al. | |
| 9,221,865 B2 | 12/2015 | Nakamura et al. | |
| 9,475,835 B2 | 10/2016 | Nakamura et al. | |
| 10,059,734 B2 | 8/2018 | Kuniyoshi et al. | |
| 10,093,645 B2 | 10/2018 | Nakamura et al. | |
| 10,385,089 B2 | 8/2019 | Kuniyoshi et al. | |
| 2002/0173482 A1 | 11/2002 | Ajani et al. | |
| 2003/0124054 A1 | 7/2003 | Toyohara et al. | |
| 2003/0138864 A1 | 7/2003 | Ishitsuka et al. | |
| 2005/0129611 A1 | 6/2005 | Toyohara et al. | |
| 2006/0142238 A1 | 6/2006 | McGuigan | |
| 2009/0069263 A1 | 3/2009 | Damha et al. | |
| 2010/0272717 A1 | 10/2010 | Evans et al. | |
| 2011/0152542 A1 | 6/2011 | Voigtlander et al. | |
| 2013/0005991 A1 | 1/2013 | Voigtlander et al. | |
| 2013/0252918 A1 | 9/2013 | McGuigan | |
| 2014/0378409 A1 | 12/2014 | Fujita et al. | |
| 2015/0011499 A1 | 1/2015 | Baba | |
| 2015/0152131 A1 | 6/2015 | Nakamura et al. | |
| 2016/0024132 A1 | 1/2016 | Nakamura et al. | |
| 2016/0355497 A1 | 12/2016 | Takeda et al. | |
| 2016/0355536 A1 | 12/2016 | Ito et al. | |
| 2016/0362389 A1 | 12/2016 | Nakamura et al. | |
| 2017/0233429 A1 | 8/2017 | Kuniyoshi et al. | |
| 2018/0079770 A1 | 3/2018 | Ye et al. | |
| 2018/0327377 A1 | 11/2018 | Nakamura et al. | |
| 2018/0360865 A1 | 12/2018 | Tanisaka et al. | |
| 2019/0192546 A1 | 6/2019 | Iwaki et al. | |
| 2020/0405752 A1 | 12/2020 | Yamada et al. | |

FOREIGN PATENT DOCUMENTS

| | | |
|---|---|---|
| CA | 2224155 C | 10/2004 |
| CN | 1615131 A | 5/2005 |
| CN | 101058557 A | 10/2007 |
| CN | 101200463 A | 6/2008 |
| CN | 101880287 A | 11/2010 |
| CN | 101896177 A | 11/2010 |
| CN | 102166190 A | 8/2011 |
| CN | 104203969 A | 12/2014 |
| EP | 0 841 344 A1 | 5/1998 |
| EP | 2 799 070 A1 | 11/2014 |
| EP | 2 832 740 A1 | 2/2015 |
| EP | 2 883 542 A1 | 6/2015 |
| EP | 2 883 866 A1 | 6/2015 |

(Continued)

OTHER PUBLICATIONS

Ettmayer et al., J. Med. Chem., 2004, 47(10), p. 2393-2404. (Year: 2004).*
Razumilava et al., Lancet, 2014, 383, p. 2168-2179. (Year: 2014).*
Yuichi Yoshimura et al., "A Facile, Alternative Synthesis of 4'-Thioarabinonucleosides and their Biological Activities", J. Med. Chem. 1997, 40(14); pp. 2177-2183.
Yuichi Yoshimura et al., A Novel Synthesis of 2'-Modified 2'-Deoxy-4'-thocytidines from D-Glucosel, J. Org. Chem., 1997, pp. 3140-3152, vol. 62.
Yuichi Yoshimura et al., "Synthetic Studies on 2'-Substituted-4'-Thiocytidine Derivatives as Antineoplastic Agents", Nucleosides & Nucleotides, 1999, pp. 815-820, vol. 18, Nos. 4&5.

(Continued)

*Primary Examiner* — Jonathan S Lau

(74) *Attorney, Agent, or Firm* — Sughrue Mion, PLLC

(57) ABSTRACT

It is an object of the present invention to provide an antitumor agent for biliary tract cancer that exhibits effects on biliary tract cancer, and a method for treating biliary tract cancer. According to the present invention, provided is an antitumor agent for biliary tract cancer, comprising 1-(2-deoxy-2-fluoro-4-thio-β-D-arabinofuranosyl)cytosine, a salt thereof, or a prodrug thereof.

7 Claims, 3 Drawing Sheets

(56) References Cited

FOREIGN PATENT DOCUMENTS

| | | |
|---|---|---|
| JP | 53-119810 A | 10/1978 |
| JP | 55-49395 A | 4/1980 |
| JP | 56-92239 A | 7/1981 |
| JP | 5-178875 A | 7/1993 |
| JP | H06-501261 A | 2/1994 |
| JP | 8-53490 A | 2/1996 |
| JP | 8-504753 A | 5/1996 |
| JP | 10-282039 A | 10/1998 |
| JP | 2003-172990 A | 6/2003 |
| JP | 2005-503358 A | 2/2005 |
| JP | 2006-335737 A | 12/2006 |
| JP | 2006-528162 A | 12/2006 |
| JP | 2007-514643 A | 6/2007 |
| JP | 4202327 B2 | 12/2008 |
| JP | 2009-538829 A | 11/2009 |
| JP | 2010-59173 A | 3/2010 |
| JP | 4719356 B2 | 7/2011 |
| JP | 2011-526242 A | 10/2011 |
| JP | 2013-514260 A | 4/2013 |
| JP | 2013/146833 | 10/2013 |
| JP | 2013/146833 A1 | 10/2013 |
| JP | 2013-540129 A | 10/2013 |
| JP | 2014/027658 A1 | 2/2014 |
| RU | 2284184 C2 | 9/2006 |
| WO | 91/04982 A1 | 4/1991 |
| WO | 94/05687 A1 | 3/1994 |
| WO | 96/01834 A1 | 1/1996 |
| WO | 97/37993 A1 | 10/1997 |
| WO | 97/38001 A1 | 10/1997 |
| WO | 97/038001 A1 | 10/1997 |
| WO | 97/49716 A1 | 12/1997 |
| WO | 99/28312 A2 | 6/1999 |
| WO | 99/43690 A1 | 9/1999 |
| WO | 02058740 A1 | 8/2002 |
| WO | 03/000200 A2 | 1/2003 |
| WO | 2004/014930 A1 | 2/2004 |
| WO | 2004/014931 A1 | 2/2004 |
| WO | 2004/027658 A1 | 4/2004 |
| WO | 2004/100891 A2 | 11/2004 |
| WO | 2004/106352 A1 | 12/2004 |
| WO | 2005/012327 A2 | 2/2005 |
| WO | 2006/073197 A1 | 7/2006 |
| WO | 2007/056596 A2 | 5/2007 |
| WO | 2007/068113 A1 | 6/2007 |
| WO | 2007/130783 A2 | 11/2007 |
| WO | 2011/074484 A1 | 6/2011 |
| WO | 2012/045999 A1 | 4/2012 |
| WO | 2013/100014 A1 | 7/2013 |
| WO | 2013/146833 A1 | 10/2013 |
| WO | 2014/027658 A1 | 2/2014 |
| WO | 2016/068341 A1 | 5/2016 |
| WO | 2016/155593 A1 | 10/2016 |
| WO | 2017/150511 A1 | 9/2017 |
| WO | 2018/043530 A1 | 3/2018 |
| WO | 2019/176984 A1 | 9/2019 |

OTHER PUBLICATIONS

Yoshimura et al., Synthesis of 2'-deoxy-2'-fluoro-4'-thioarabinonucleosides as potential antitumor and antiviral agents from D-glucose, Nucleic Acids Symposium Series, No. 35, pp. 15-16, 1996 (2 pages total).

Yoshimura et al., A Novel Synthesis of New Antineoplastic 2'-Deoxy-2'-substituted-4'-thiocytidines, Journal of Organic Chemistry, vol. 61, No. 3, pp. 822-823, 1996 (2 pages total).

Yoshimura et al. "An Alternative Synthesis of the Antineoplastic Nucleoside 4'-ThioFAC and Its Application to the Synthesis of 4'-ThioFAG and 4'-Thiocytarazid", J.Org Chem., vol. 64, Jun. 14, 1999, pp. 7912-7920 (9 pages total).

Wang et al. "A Practical Synthesis of Sugar-Derived Cyclic Nitrones: Powerful Synthons for the Synthesis of Iminosugars", Synlett Letter, 2010, No. 3, pp. 488-492 (5 pages total)93.

Vorbruggen et al., "Synthesis of nucleosides" Org. Reactions (2000), pp. 55.

Ototani et al., "Preparation and Antitumor Activity of 4'-Thio Analogs of 2,2,-Anhydro-1-β-D-arabinofuranosylcytosine," Journal of Medicinal Chemistry, 1974, vol. 17, No. 5, pp. 535-537 (3 pages total).

Thomas B. Mercer et al., Looking glass inhibitors: both enanthiomeric N-benzyl derivatives of 1,4-dideoxy-1,4-imino-D-lyxitol [a potent competitive inhibitor of a-D-glactosidase ] and of 1-4-dideoxy-1,4-imino-L-lyxitol [a weak competitive inhibitor of a-D-glactosidase] inhibit naringinase, an α-L-rhamnosidase competitively, Tetrahedron: Asymmetry, 2009, pp. 2368-2373, vol. 20, No. 20.

Tann et al., Fluorocarbohydrates in Synthesis. An Efficient Synthesis of 1-(2-Deoxy-2-fluoro-ß-D-arabino-furanosyl)-5-iodouracil (ß-FIAU) and 1-(2-Deoxy-2-fluoro-ß-D-arabinofuranosyl) thymine (ß-FMAU), Journal of Organic Chemistry, American Chemical Society, vol. 50, No. 19, 1985. pp. 3644-3647 (4 pages total).

Takashi Komine et al., "Synthesis and Structure-Activity Relationship Studies of Highly Potent Novel Oxazolidinone Antibacterials", J. Med. Chem., 2008, pp. 6558-6562, 2008, vol. 51, No. 20.

Stephanie A. Hartsel et al., "Synthesis of 9-(4-Thioxylofuranosyl) adenine via a Novel Glycosylation Reaction", Tetrahedron Letters 39 (1998) pp. 205-208.

Shinji Miura et al., "Potent antitumor effect of 1-(2-deoxy-2-fluoro-4-thio-ß-D-arabinofuransoyl)cytsine on peritoneal dissemination models of gastrointestinal cancers", Oncology Reports, 2002, pp. 1319-1322, vol. 9, No. 6.

Shinji Miura et al., "Comparison of 1-(2-deoxy -2fluoro-4-thio-ß-D-arabinofuranosyl)cytosine with gemcitabine in its antitumor activity", Cancer Letters, 1999, pp. 177-182, vol. 144.

Shinji Miura et al., "Antitumor activity of a novel orally effective nucleoside, 1-(2-deoxy-2-fluoro-4-thio-ß-D-arabinofuranosyl)cytosine", Cancer Letters, 1998, pp. 103-110, vol. 129.

Ronald C. Horton Jr. et al, "Aldehyde-Terminated Self-Assembled Monolayers on Gold: Immobilization of Amines onto Gold Surfaces", J. Am. Chem. Soc., 1997, vol. 119; pp. 12980-12981.

R. M. Rowell et al., "Derivatives of a-D-Glucothiopyranose", J. Org. Chem., 1996, vol. 31; pp. 1514-1516.

Partial European Search Report dated Nov. 24, 2010 issued in European Application No. 10163406.

Oscar Varela et al., "First Synthesis of Aldopentono-1,4-thiolactones", J. Org. Chem., 1993, pp. 7860-7864, vol. 58, No. 27.

Official Action dated Jul. 1, 2015 issued in Chinese patent application No. 201380016308.9.

Office Action dated Nov. 8, 2012 in U.S. Appl. No. 13/606,746 (now U.S. Pat. No. 8,420,831).

Notices of Allowance and Allowability dated Nov. 8, 1999, in U.S. Appl. No. 08/973,529 (now U.S. Pat. No. 6,147,058).

Office Action in Taiwanese application No. 99142198 dated Sep. 11, 2014.

Office Action issued in Chinese application No. 201380042642.1 dated Aug. 2, 2017.

Office Action issued in European application No. 10801279.0 dated Jun. 4, 2013.

Masajiro Kawana et al., "The Synthesis of 2',3'-Diodexycytidene and Its 2'-Azido Analogue Applications of the Deoxygenative [1,2]-Hydride Shift of Sulfonates with Mg(OMe)2-NaBH4", Chemistry Letters, 1987, pp. 2419-2422.

Miura et al., "Suppression of Peritoneal Dissemination by 4'-thio-FAC," Oncology Reports, vol. 9, No. 6, Nov.-Dec. 2002, pp. 1319-1322 (9 pages total).

Magdalena Slusarczyk et al., "Application of ProTide Technology to Gemcitabine: A Successful Approach to Overcome the Key Cancer Resistance Mechanisms Leads to a New Agent (NUC-1031) in Clinical Development", J. Med. Chem, 2014, pp. 1531-1542, vol. 57.

Lak Shin Jeong et al., "N6-Substituted D-4'-Thioadenosine-5'-methyluronamides: Potent and Selective Agonists at the Human A3 Adenosine Receptor", J. Med. Chem., 2003, pp. 3775-3777, vol. 46, No. 18.

Karrer, Org. Chem. 2nd Ed. (1996), pp. 92-102.

King, "Bioisosteres, Conformational Restriction, and Pro-drugs—Case History: An Example of a Conformational Restriction Approach," Med. Chem., Principle and Practice (1994), pp. 206-208, Chapter 14.

(56) References Cited

OTHER PUBLICATIONS

John A. Secrist III et al. "Synthesis and Biological Activity of 2'-Deoxy-4'-thio Pyrimidine Nucleosides", J. Med. Chem. 1991, 34, No. 8 (pp. 2361 -2366).
Jeong, et al., Participation of sulfur occurred during the Mitsunobu reaction: synthesis of novel isodideoxythionucleosides, J. Chem. Soc., Perkin Trans. 1, pp. 3325-3326, 1998 (2 pages total).
International Search Report issued in PCT/JP2013/0711871, dated Nov. 26, 2013.
Hyunah Choo et al., "Synthesis, Anti-HIV Activity, and Molecular Mechanism of Drug Resistance of L-2',3,-Didehydro-2,,3,-dideoxy-2,-fluoro-4'-thionucleosides", J. Med. Chem., 2003, pp. 389-398, vol. 46, No. 3.
Hayato Fujita et al., "Gene Expression Levels as Predictive Markers of Outcome in Pancreatic Cancer after Gemcitabine-Based Adjuvant Chemotherapy1,2", Neo Plasia, Oct. 2010, pp. 807-817, vol. 12, No. 10.
Cox, J.M., et al., "Cyclic Hemithioacetals: Analogues of Thiosugars with Sulphur in the Ring", J. Chem. Soc., Section C, 1967, pp. 1130-1134.
Chinese Office Action for Application No. 201280042642.1, dated Nov. 2, 2015.
David Baker et al., "Large-scale preparation of D-allose: observations on the stereoselectivity of the reduction of 1,2:5,6-di-O-isopropylidene-α-D-ribo-hexofuranos-3-ulose hydrate", Carbohydrate Research, 1972, pp. 192-197, vol. 24.
Feng Zheng et al., "Synthesis of L-β-3'-Deoxy-3', 3'-difluoro-4'-thionucleosides", Organic Letters, vol. 8, No. 26, pp. 6083-6086, 2006, 4 pages total.
Office Action dated Apr. 17, 2019, issued by the State Intellectual Property Office of People's Republic of China in Chinese Application No. 201610838593.8, corresponding to subject-matter related U.S. Appl. No. 16/045,047.
Office Action issued Nov. 5, 2020 in U.S. Appl. No. 16/286,930.
International Preliminary Report on Patentability dated Mar. 5, 2019 in International Application No. PCT/JP2017/031074, corresponding to U.S. Appl. No. 16/286,930.
International Search Report for PCT/JP2017/031074 dated Oct. 24, 2017 (PCT/ISA/210), corresponding to U.S. Appl. No. 16/286,930.
Written Opinion dated Oct. 24, 2017 in International Application No. PCT/JP2017/031074, corresponding to U.S. Appl. No. 16/286,930.
Miura et al., "The Antitumor Mechanism of I-(2-Deoxy-2-fluoro-4-thio-β-D-arabinofuranosyl)-cytosine: Effects of Its Triphosphate on Mammalian DNA Polymerases", Japanese Journal of Cancer Research, vol. 92, No. 5, pp. 562-567, May 2001, 6 pages total.
Extended European Search Report dated Aug. 7, 2019 issued by the European Patent Office in application No. 17846534.0, corresponding to U.S. Appl. No. 16/286,930.
Daniel D. Von Hoff, et al., "Increased Survival in Pancreatic Cancer with nab-Paclitaxel plus Gemcitabine", The New England Journal of Medicine, vol. 369, No. 18, pp. 1691-1703, (Oct. 31, 2013).
William J. Gradishar, et al., "Phase III Trial of Nanoparticle Albumin-Bound Paclitaxel Compared With Polyethylated Castor Oil-Based Paclitaxel in Women With Breast Cancer", Journal of Clinical Oncology, vol. 23, No. 31, pp. 7794-7803, (Nov. 1, 2005).
Examination report dated Aug. 20, 2019 issued by the Australian Intellectual Property Office in application No. 2017319260, corresponding to U.S. Appl. No. 16/286,930.
C. Khanna et al., "A Review of Paclitaxel and Novel Formulations Including Those Suitable for Use in Dogs", Journal of Veterinary Internal Medicine, vol. 29, 2015, pp. 1006-1012 (7 pages total).
Communication dated Dec. 23, 2019 from the Intellectual Property of India in application No. 201947007839, corresponding to U.S. Appl. No. 16/286,930.
Communication dated Jan. 21, 2020, from the Japanese Patent Office in Application No. 2018-537328, corresponding to U.S. Appl. No. 16/286,930.
Communication dated Oct. 14, 2019 from the Russian Patent and Trademark Office in application No. 2019105574, corresponding to U.S. Appl. No. 16/286,930.

D.A. Kharkevich., Pharmacology, Moscow, Meditsina, 1987, pp. 46-48, (3 pages total).
Deborah Zajchowski et al., "Anti-tumor efficacy of the nucleoside analog I-(2-deoxy-2-fluoro-4-thio-β-D-arabinofuranosyl) cytosine (4'-thio-FAC) in human pancreatic and ovarian xenograft models.", Proc Amer Assoc Cancer Res, Apr. 2004, vol. 45, (5 pages total).
Mashkovskiy M.D., "Lekarstvennyye sredstva [Drugs]", 14-ed., vol. 1, Moscow, pp. 11, 2001 (2 pages total).
Anna Cividalli et al., "Enhancement of Radiation Response by Paclitaxel in Mice According to Different Treatment Schedules", International Journal of Radiation Oncology Biol. Phys., 1998, vol. 40, No. 5, pp. 1163-1170 (total 8 pages).
Wenger A. Pharmacological incompatibility, Bulletin of Siberian Medicine, 2003, n3, pp. 49-56 (total 8 pages).
Akamatsu et al., "Action mechanism of cancer pharmacotherapeutic agents, Cytotoxic antineoplastic agent, Platinum preparation, alkylating agent, and anticancer antibiotics", Japanese Journal of Clinical Medicine (special issue), 2014, vol. 27, suppl. 2, pp. 124-126.
Communication dated Mar. 26, 2020 from the Russian Patent Office in RU Application No. 2019105574/04, corresponding to U.S. Appl. No. 16/286,930.
Communication dated May 7, 2020 from the European Patent Office in EP Application No. 17846534.0, corresponding to U.S. Appl. No. 16/286,930.
International Search Report dated May 21, 2019 in International Application No. PCT/JP2019/010169, corresponding to U.S. Appl. No. 17/018,413.
Mima et al., "FF-10502, an Antimetabolite with Novel Activity on Dormant Cells, is Superior to Gemcitabine for Targeting Pancreatic Cancer Cells", The Journal of Pharmacology and Experimental Therapeutics, 2018, vol. 366, No. 1, pp. 125-135.
Written Opinion of the International Searching Authority dated May 21, 2019 in International Application No. PCT/JP2019/010169, corresponding to U.S. Appl. No. 17/018,413.
Chikuma et al., "Current Status and Future Perspectives of Platinum Antitumor Drugs", Yakugaku Zasshi, 2008, vol. 128, No. 3, pp. 307-316.
Heinemann et al., "Randomized Phase III Trial of Gemcitabine Plus Cisplatin Compared With Gemcitabine Alone in Advanced Pancreatic Cancer", Journal of Clinical Oncology, 2006, vol. 24, No. 24, pp. 3946-3952 (13 pages total).
Poplin et al., "Phase III, Randomized Study of Gemcitabine and Oxaliplatin Versus Gemcitabine (fixed-dose rate infusion) Compared With Gemcitabine (30-minute infusion) in Patients With Pancreatic Carcinoma E6201: A Trial of the Eastern Cooperative Oncology Group", Journal of Clinical Oncology, 2009, vol. 27, No. 23, pp. 3778-3785 (8 pages total).
Communication dated Jul. 31, 2020, from the Chinese Patent Office in Application No. 201780053185.4, corresponding to U.S. Appl. No. 16/286,930.
Yu Yongqiang, "Modern hospital diagnosis and treatment routine (internal medicine, pediatrics)", Sep. 30, 2012, pp. 865-866 (4 pages total).
Zheng Baoguo, "Modern clinical oncology", Apr. 30, 2013, p. 558 (1 page).
Office Action dated Nov. 1, 2019 in U.S. Appl. No. 16/286,930.
Office Action dated May 4, 2020 in U.S. Appl. No. 16/286,930.
Office Action dated Aug. 25, 2020 from the Japanese Patent Office in Japanese Application No. 2018-537328, corresponding to U.S. Appl. No. 16/286,930.
International Preliminary Report on Patentability dated Sep. 15, 2020 in International Application No. PCT/JP2019/010169, corresponding to U.S. Appl. No. 17/018,413.
Zajchowski et al., "Anti-tumor efficacy of the nucleotide analog 1-(2-deoxy-2-fluoro-4-thio-β-D-arabinofuranosyl) cytosine (4'-thio-FAC) in human pancreatic and ovarian tumor xenograft models", Int. J. Cancer, 2005, vol. 114, pp. 1002-1009 (8 pages total).
Kolinsky et al., "A Case Series of Patients with Pancreatic Cancer and Cholangiocarcinoma Treated with nab-Paclitaxel at a Single Institution", Journal of Cancer Therapy, 2014, vol. 5, pp. 605-610 (6 pages total).
U.S. Appl. No. 16/286,930, filed Feb. 27, 2019 (Iwaki).
U.S. Appl. No. 17/018,413, filed Sep. 11, 2020 (Yamada).

(56) References Cited

OTHER PUBLICATIONS

U.S. Appl. No. 16/286,930, Pending.
U.S. Appl. No. 17/018,413, Pending.
U.S. Appl. No. 15/581,834, Patented as U.S. Pat. No. 10,059,734.
U.S. Appl. No. 16/037,375, Patented as U.S. Pat. No. 10,385,089.
International Search Report dated May 1, 2018 in International Application No. PCT/JP2018/007772.
Written Opinion of the International Searching Authority dated May 1, 2018 in International Application No. PCT/JP2018/007772.
International Preliminary Report on Patentability dated Aug. 1, 2019 in International Application No. PCT/JP2018/007772.
Miura et al., "Antitumor activity of a novel orally effective nucleoside, 1-(2-deoxy-2-fluoro-4-thio-β-D-arabinofuranosyl)cytosine", Cancer Letters, 1998, vol. 129, pp. 103-110 (8 pages total).
Miura et al., "Comparison of 1-(2-deoxy-2-fluoro-4-thio-(3-D-arabinofuranosyl)cytosine with gemcitabine in its antitumor activity", Cancer Letters, 1999, vol. 144, pp. 177-182 (6 pages total).
Miura et al., "Potent antitumor effect of 1-(2-deoxy-2-fluoro-4-thio-β-D-arabinofuranosyl)cytosine on peritoneal dissemination models of gastrointestinal cancers", Oncology Reports, 2002, vol. 9, pp. 1319-1322 (4 pages total).
American Association for Cancer Research (AACR) Annual Meeting, Apr. 1-5, 2017, Washington, DC (48 pages total).
Mima et al., "In vitro and in vivo evaluation of FF-10502-01, a new pyrimidine nucleoside analogue", AACR Annual Meeting, Apr. 5, 2017 (1 page total).
Suzuki et al., "Evaluation of FF-10502-01, a new pyrimidine nucleoside analogue, in pancreatic (PANC) patient-derived xenograft (PDX) models compared to gemcitabine and in combination with nab-paclitaxel", AACR Annual Meeting, Apr. 5, 2017 (2 pages total).
Falchook et al., "First-in-human phase 1 trial of pyrimidine antimetabolite FF-10502-01 in patients with advanced cancer", AACR Annual Meeting, Apr. 4, 2017 (1 page total).
Janku et al., "Preliminary Activity of FF-10502-01 in Patients with Refractory Advanced Cholangiocarcinoma", Annual Conference of cholangiocarcinoma foundation, Jan. 31, 2018, Salt Lake City, USA (1 page total).
Saeki et al., "A novel antimetabolite, FF-10502-01 exhibits potent antitumor activity via inhibition of both DNA replication and DNA damage repair in solid tumor cells", AACR 2018 Abstract 3350, Apr. 15, 2018, Chicago, USA (1 page total).
Communication dated Nov. 25, 2020 from the European Patent Office in Application No. 17846534.0, corresponding to U.S. Appl. No. 16/286,930.
Office Action dated Nov. 5, 2020 from the U.S. Patent Office in U.S. Appl. No. 16/286,930.
Office Action dated Mar. 12, 2021 from the China National Intellectual Property Administration in CN Application No. 201780053185.4, corresponding to U.S. Appl. No. 16/286,930.
Dilruba et al., "Platinum-based drugs: past, present and future", Cancer Chemother Pharmacol, 2016, vol. 77, pp. 1103-1124 (22 pages total).
Extended European Search Report dated Apr. 7, 2021 in European Application No. 19767269.4, corresponding to U.S. Appl. No. 17/018,413.
Office Action dated Mar. 30, 2021 in corresponding Australian Application No. 2018404329.
Office Action dated Mar. 31, 2021 in Canadian Application No. 3,035,334, corresponds to U.S. Appl. No. 16/286,930.
Yuichi Yoshimura et al., "A Facile, Alternative Synthesis of 4'-Thioarabinonucleosides and their Biological Activities", J. Med. Chern. 1997, 40(14); pp. 2177-2183.
Yuichi Yoshimura et al., A Novel Synthesis of 2'-Modified 2'-Deoxy-4'-thocytidines from D-Glucose1, J. Org. Chern., 1997, pp. 3140-3152, vol. 62.
Yuichi Yoshimura et al., "Synthetic Studies On 2'-Substituted-4'-Thiocytidine Derivatives as Antineoplastic Agents", Nucleosides & NUCLEOTIDES, 1999, pp. 815-820, vol. 18, Nos. 485.
Yuichi Yoshimura et al., "An alternative synthesis of antineoplastic nucleoside 4'-thioFAC", Nucleic Acids Symposium Series No. 39, 1998, pp. 11-12.
Yuichi Yoshimura et al., "An Alternative Synthesis of Antineoplastic 4'-Thiocytidine Analogue 4'-ThioFAC", Tetrahedron Letters, 1999, pp. 1937-1940, vol. 40.
Yuichi Yoshimura e al., "Synthesis and Biological Activities of 2'-Deoxy-2'fluoro-4'thioarabinofuranosylpyrimidine and -Purine Nucleosides", Bioorganic & Medicinal Chemistry, 2000, pp. 1545-1558, vol. 8.
Yoshimura et al., Synthesis of 2' -deoxy-2' -fluoro-4' -thioarabinonucleosides as potential antitumor and antiviral agents from D-glucose, Nucleic Acids Symposium Series, No. 35, pp. 15-16, 1996 (2 p. total).
Yoshimura et al., A Novel Synthesis of New Antineoplastic 2'-Deoxy-2' -substituted -4'-thiocytidines, Journal of Organic Chemistry, vol. 61, No. 3, pp. 822-823, 1996 (2 p. total).
Yoshimura et al. "An Alternative Synthesis of the Antineoplastic Nucleoside 4'-ThioFAC and Its Application to the Synthesis of 4'-ThioFAG and 4'-Thiocytarazid", J.Org Chern., vol. 64, Jun. 14, 1999, pp. 7912-7920 (9 p. total).
Y. Yoshimura et al., Nucleic Acids Symposium Series, No. 35, pp. 15-16 (1996).
Y. Yoshimura et al., Journal of Organic Chemistry, vol. 61, No. 3, pp. 822-823 (1996).
Wu-Bao Wang et al., "A Practical Synthesis of Sugar-Derived Cyclic Nitrones: Powerful Synthons for the Synthesis of Iminosugars", Synlett, 2010, pp. 488-492, No. 3.
Written Opinion for PCT/JP2015/080885, dated Feb. 2, 2016.
William Plunkett et al., "Preclinical characteristics of gemcitabine", Anti-Cancer Drugs, 1995, pp. 7-13, vol. 6, Suppl. 6.
Watts et al., "2'-Fluoro-4'-thioarabino-modified oligonucleotides: conformational switches linked to siRNA activity" Nuclei. Acids Res. (2007) vol. 35(5), pp. 1441-1451.
Watts et al., "Synthesis and Conformational Analysis of 2'-Fluoro-5-methyl-4'-thioarabinouridine (4'S-FMAU)", Journal of Organic Chemistry, vol. 71, No. 3, Jan. 22, 2006, pp. 921-925, XP002606716.
Wang et al. "A Practical Synthesis of Sugar-Derived Cyclic Nitrones: Powerful Synthons for the Synthesis of Iminosugars", Synlett Letter, 2010, No. 3, pp. 488-492 (5 p. total)93.
Vorbruggen et al., "Synthesis of nucleosides" Org. Reactions (2000), p. 55.
Vjera Pejanovic et al., "Synthesis and Biological Evaluation of Some Novel 4'-Thio-L-ribonucleosides with Modified Nucleobase Moieties", Bioorganic & Medicinal Chemistry Letters, 2003, 13(11) pp. 1849-1852.
Zefirova, O.N., et al., "On history of emergence and development of bioisoterism concept", Moscow University Herald, Series 2, Chemistry, 2002, T. 43, No. 4, pp. 251-256 (6 pages).
Ototani et al., "Preparation and Antitumor Activity of 4'-Thio Analogs of 2,2,-Anhydro-1-(3-D-arabinofuranosylcytosine," Journal of Medicinal Chemistry, 1974, vol. 17, No. 5, pp. 535-537 (3 p. total).
Thomas B. Mercer et al., Looking glass inhibitors: both enanthiomeric N-benzyl derivatives of 1,4-dideoxy-1,4-imino-D-lyxitol [a potent competitive inhibitor of a-D-glactosidase] and of 1-4-dideoxy-1,4-imino-L-lyxitol [a weak competitive inhibitor of a-D-glactosidase] inhibit naringinase, an a-L-rhamnosidase competitively, Tetrahedron: Asymmetry, 2009, pp. 2368-2373, vol. 20, No. 20.
Tann et al., Fluorocarbohydrates in Synthesis. An Efficient Synthesis of 1-(2-Deoxy-2-fluoro-B-D-arabino-furanosyl)-5-iodouracil (B-FIAU) and 1-(2-Deoxy-2-fluoro-B-D-arabinofuranosyl) thymine (B-FMAU), Journal of Organic Chemistry, American Chemical Society, vol. 50, No. 19, 1985. pp. 3644-3647 (4 pages total).
Takashi Komine et al., "Synthesis and Structure-Activity Relationship Studies of Highly Potent Novel Oxazolidinone Antibacterials", J. Med. Chern., 2008, pp. 6558-6562, 2008, vol. 51, No. 20.
Stephen M. Berge et al., "Pharmaceutical Salts", Journal of Pharmaceutical Sciences, Jan. 1977, pp. 1-19, vol. 66, No. 1.
Stephanie A. Hartsei et al., "Synthesis of 9-(4-Thioxylofuranosyl) adenine via a Novel Glycosylation Reaction", Tetrahedron Letters 39 (1998) pp. 205-208.

(56) References Cited

OTHER PUBLICATIONS

Shinji Miura et al., "Potent antitumor effect of 1-(2-deoxy -2-fluoro-4-thio-(3-D-arabinofuransoyl)cytsine on peritoneal dissemination models of gastrointestinal cancers", Oncology Reports, 2002, pp. 1319-1322, vol. 9, No. 6.
Shinji Miura et al., "Comparison of 1-(2-deoxy -2fluoro-4-thio-(3-D-arabinofuranosyl)cytosine with gemcitabine in its antitumor activity", Cancer Letters, 1999, pp. 177-182, vol. 144.
Shinji Miura et al., "Antitumor activity of a novel orally effective nucleoside, 1-(2-deoxy-2-fluoro-4-thio-]3-D-arabinofuranosyl)cytosine", Cancer Letters, 1998, pp. 103-110, vol. 129.
Russian Office Action for Application No. 2015108790, dated Apr. 25, 2016.
Ronald C. Horton Jr et al., "Aldehyde-Terminated Self-Assembled Monolayers on Gold: Immobilization of Amines onto Gold Surfaces", J. Am. Chem. Soc., 1997, vol. 119; p. 12980-12981.
Raoul, S., et al., " 1H, 13C and 15N Nuclear magnetic resonance analysis and chemical features of the two main radical oxidation products of 2'-'deoxyguanosine: oxazolone and imidazolone nucleosides", J. Chemical So., Perkin Trans. 2, 1996, Issue 3, pp. 371-381 (11 pages).
R. M. Rowell et al., "Derivatives of a-D-Glucothiopyranose", J. Org. Chern., 1996, vol. 31; pp. 1514-1516.
Peter Haeberli et al., "Syntheses of 4,-thioribonucleosides and thermodynamic stability and crystal structure of RNA oligomers with incorporated 4'-thiocytosine," Nucleic Acids Research, 2005, vol. 33, No. 13; pp. 3965-3975.
PCT International Preliminary Report on Patentability (IPRP), dated Jun. 19, 2012 for PCT International Application No. PCT/JP2010/072182.
Paul Karrer, "Organic Chemistry", 2nd English Edition, Elsevier Publ. Comp., Inc., NY, pp. 92-102 (1946).
Partial Supplemental European Search Report issued in European Application No. 13879640.4, dated Feb. 16, 2016.
Partial European Search Report dated Nov. 24, 2010 issued in European U.S. Appl. No. 10/163,406.
Ototani et al., "Preparation and Antitumor Activity of 4'-Thio Analogs of 2/2'-Anhydro-1-B-D-arabinofuranosylcytosine," Journal of Medicinal Chemistry, 1974, vol. 17, Nos. pp. 535-537 (3 p. total).
Oscar Varela et al., "First Synthesis of Aldopentono-1,4-thiolactones", J. Org. Chern., 1993, pp. 7860-7864, vol. 58, No. 27.
Official Action dated Sep. 13, 2016 issued in Israeli patent application No. 234222.
Official Action dated Oct. 5, 2015 issued in Australian patent application No. 2013241341.
Official Action dated Jan. 11, 2017 issued in Korean Patent Application No. 10-2015-7003655 with its English machine translation.
Official Action dated Jan. 16, 2 017 issued in Chinese Patent Application No. 201380042642.1.
Official Action dated Jan. 28, 2015 issued in New Zealand Patent Application No. 701245.
Official Action dated July 1, 2 015 issued in Chinese patent application No. 201380016308.9.
Official Action dated Mar. 19, 2015 issued in Singapore Patent Application No. 11201406080V.
Official Action dated Mar. 21, 2016 issued in Russian Patent Application 2014143277/04.
Official Action dated Mar. 29, 2016 issued in Canadian Patent Application No. 2,865,742.
Official Action dated May 25, 2016 issued in Taiwanese Patent Application No. 102110915.
Official Action dated Nov. 2, 2015 issued in Canadian Patent Application No. 2,880,794.
Official Action dated Nov. 5, 2015 issued in Russian Patent Application No. 2014143277.
Official Action dated Oct. 25, 2016 issued in Korean patent application No. 10-2014-7030209.
Office Action issued in Korean application No. 10-2012-7018741 dated Dec. 1, 2016.

Office Action issued in Russian application No. 2012130422 dated Jan. 22, 2015.
Office Action issued in Singapore application No. 2012044368 dated Jun. 11, 2014.
Office Action issued in Vietnamese application No. 1-2012-02041 dated Jul. 4, 2013.
Office Action issued in Vietnamese application No. 1-2012-02041 dated Mar. 7, 2014.
Office Action dated Aug. 11, 2016 in U.S. Appl. No. 14/498,334.
Office Action dated Novembers, 2012 in U.S. Appl. No. 13/606,746 (now U.S. Pat. No. 8,420,831).
Official Action dated Apr. 7, 2015 issued in Japanese Patent Application No. 2014-507938.
Official Action dated Sep. 30, 2016 issued in Taiwanese patent application No. 102110915.
Official Action dated Aug. 18, 2016 issued in Canadian Patent Application No. 2,880,794.
Official Action dated Aug. 21, 2015 issued in New Zealand patent application No. 701245.
Official Action dated Dec. 29, 2016 issued in Russian Patent Application No. 2015108790.
Notice of Allowance dated Feb. 15, 2017 in U.S. Appl. No. 14/498,334.
Notice of Allowance issued in U.S. Appl. No. 14/873,966, dated May 26, 2016.
Notice of Final Rejection dated Apr. 3, 2017 issued in Korean patent application No. 10-2014-7030209.
Notice of Final Rejection dated Nov. 21, 2016 issued in Korean Patent Application No. 10-2015-7003655.
Notices of Allowance and Allowability dated Novembers, 1999, in U.S. Appl. No. 08/973,529 (now U.S. Pat. No. 6,147,058).
Office Action in Taiwanese U.S. Appl. No. 99/142,198 dated Sep. 11, 2014.
Office Action issued in Australian application No. 2010331367 dated Jul. 25, 2016.
Office Action issued in Canadian application No. 2,784,399 dated Oct. 6, 2016.
Office Action issued in Chinese application No. 201380042642.1 dated August 2, 2 017.
Office Action issued in European application No. 10801279.0 dated Dec. 16, 2 013.
Office Action issued in European application No. 10801279.0 dated June 4, 2 013.
Office Action issued in European application No. 14177042.0 dated Aug. 19, 2 015.
Martin W. Bredenkamp et al., "Stannylene Directed Selective Acylation of Some Open-Chain L-Arabinose Derivatives", Tetrahedron Letters, 1990, 31(19) pp. 2759-2762.
Masajiro Kawana et al., "The Synthesis of 2',3'-Diodexycytidene and Its 2'-Azido Analogue Applications of the Deoxygenative [1,2]-Hydride Shift of Sulfonates with Mg(OMe)2-NaBH4", Chemistry Lei Iers, 1987, pp. 2419-2422.
Mayumi Takahashi et al., "Synthesis and crystal structure of 20-deoxy-20-fluoro-40-thioribonucleosides: substrates for the synthesis of novel modified RNAs", Tetrahedron, 2008, pp. 4313-4324, vol. 64.
Miura et al., "Suppression of Peritoneal Dissemination by 4'-thio-FAC," Oncology Reports, vol. 9, No. 6, November - Dec. 2002, pp. 1319-1322 (9 p. total).
Naveen K. Khare et al., "Synthesis of 4-deoxy-4-thioarabinofuranosyl disaccharides, analogs of Mycobactrial arabinoglactan", Indian Journal of Chemistry, Nov. 2008, pp. 1748-1752, vol. 47B.
Office Action issued in U.S. Appl. No. 14/873,966, dated Feb. 8, 2016.
Office Action issued in U.S. Appl. No. 14/621,119, dated Mar. 24, 2015.
Notice of Allowance dated Aug. 30, 2012 in U.S. Appl. No. 12/959,735 (now U.S. Pat. No. 8,329,925).
Larry W. Hertel et al., "Evaluation of the Antitumor Activity of Gemcitabine (2',2' -Difluoro-2' -deoxycytidine)", Cancer Research, Jul. 15, 1990, pp. 4417-4422, vol. 50.
Magdalena Slusarczyk et al., "Application of ProTide Technology to Gemcitabine: A Successful Approach to Overcome the Key

(56) References Cited

OTHER PUBLICATIONS

Cancer Resistance Mechanisms Leads to a New Agent (NUC-1031) in Clinical Development", J. Med. Chern, 2014, pp. 1531-1542, vol. 57.
Koen VANHESSCHE et al., "L-Ribulose A: Novel Chiral Pool Compound", Tetrahedron Letters, pp. 2337-2340, 1990, vol. 3, No. 16.
Office Action for Korean Application No. 10-2015-7003655, dated May 12, 2016.
Lak Shin Jeong et al., "N6-Substituted D-4'-Thioadenosine-5'-methyluronamides: Potent and Selective Agonists at the Human A3 Adenosine Receptor", J. Med. Chern., 2003, pp. 3775-3777, vol. 46, No. 18.
Karrer, Org. Chern. 2nd Ed. (1996), pp. 92-102.
King, "Bioisosteres, Conformational Restriction, and Pro-drugs - Case History: An Example of a Conformational Restriction Approach," Med. Chern., Principle and Practice (1994), pp. 206-208, Chapter 14.
Karmal N. Tiwari et al., "Synthesis and Biological Activity of 4'-Thio-L-Xylofuranosyl Nucleosides", Nucleosides, Nucleotides & Nucleic Acids, 2001, pp. 743-746, vol. 20 nos.4-7.
Kamal N. Tiwari et al., "The Synthesis and Biological Activity of 1-(2-Deoxy-4-Thio-β-L-Threo-Pentofuranosyl) Thymine", Nucleosides & Nucleotides, 12(8), pp. 841-846 (1993).
Kamal N. Tiwari et al., "Synthesis and Anti-Cancer Activity of Some Novel 5-Azacytosine Nucleosides", Nucleosides, Nucleotides & Nucleic Acids, 2003, 22(12), pp. 2161-2170.
Junji Fujita et al., "Synthesis of thiosaccharides employing the Pummerer rearrangement of tetrahydrothiopyran oxides", Tetrahedron 2004, vol. 60, No. 32, pp. 6829-6851.
Johan Fanton e al., "Enzymatic and Organocatalyzed Asymmetric Aldolization Reactions for the Synthesis of Thiosugar Scaffolds", European Journal of Organic Chemistry, 2012 pp. 203-210.
John A. Secrist III et al. "Synthesis and Biological Activity of 2' - Deoxy - 4' - thio Pyrimidine Nucleosides", J. Med. Chern. 1991, 34, No. 8 (pp. 2361-2366).
Jeong, et al., The Stereochemical Outcome of the DAST Fluorination of 4'-Thipyrimidine Nucleosides with "Up" Hydroxyl Groups is Controlled by the Oxidation State of the Sulfur Atom, Chemistry Letters, pp. 301-302, 1995. (2 pages total).
Jeong et al., Unanticipated Retention of Configuration in the DAST Fluorination of Deoxy-4' -thiopyrimidine Nucleosides with "Up" Hydroxyl Groups. Tetrahedron Letter, vol. 35, No. 41, pp. 7569-7572, 1994. (4 pages total).
Jeong et al., Tetrahedron Letters, 35(41):7569-7572, 1994.
Jeong et al., Tetrahedron Letters, 35(41):7573-7576, 1994.
Jeong et al., Facile Fluorination of Deoxy-4'-thiopyrimidine Nucleosides with "Down" Hydroxyl Groups. Retention of Configuration After Fluoride Opening of the Quartenized N3-MEM Anhydronucleosides, Tetrahedron Letters, vol. 35, No. 41, pp. 7573-7576,1994 (4 pages total).
Jeong, et al., Participation of sulfur occurred during the Mitsunobu reaction: synthesis of novel isodideoxythionucleosides, J. Chern. Soc., Perkin Trans. 1, pp. 3325-3326, 1998 (2 pages total).
J. Allen Miller et al., "2,2'-Anhydro-4'-Thionucleosides: Precursors for2'-Azido- and 2'- Chloro-4'-thionucleosides and for a Novel Thiolane to Thietane Rearrangement", Nucleosides, Nucleotides and Nucleic Acids, vol. 19, No. 9, Sep. 24, 2000, pp. 1475-1486, XP055207502.
Office Action for Japanese Application No. 2014-563560 dated Mar. 1, 2016.
Jean-Baptiste et al. "Synthesis of 2',3'-Dideoxy-2'-Fluoro-4'-Thionucleosides from a Fluoroxanthate", Synlett, Jan. 8, 2008, No. 6, pp. 817-820 (5 pages total).
International Search Report and Written Opinion for PCT/JP2013/058896, dated Jun. 4, 2013.
International search Report for PCT/JP2015/080885, dated Feb. 2, 2016.
International Search Report issued in PCT/JP2013/071871, mailed on Nov. 26, 2013.

International Preliminary Report on Patentability and Translation of Written Opinion dated Oct. 9, 2014 from the International Bureau in International application No. PCT/JP2013/058896.
International Preliminary Report on Patentability with a Translation of Written Opinion issued from the International Bureau in International Application No. PCT/JP2015/080885, dated May 11, 2017.
International Search Report and Written Opinion for PCT/JP2010/072182, dated Apr. 29, 2011.
International Preliminary Report on Patentability and Written Opinion of the International Searching Authority (forms PCT/IB388, PCT/373, PCT/ISA 237 and PCT/IB/326), dated Feb. 26, 2015, for International Application No. PCT/JP2013/071871, along with English translation.
Hyunah Choo et al., "Synthesis, Anti-HIV Activity, and Molecular Mechanism of Drug Resistance ofL-2',3,-Didehydro-2,,3,-dideoxy-2,-fluoro-4'-thionucleosides", J. Med. Chern., 2003, pp. 389-398, vol. 46, No. 3.
Hiroshi Satoh et al., "Synthesis of L-Enantiomers of 4' • Thioarabinofuranosyl Pyrimidine Nucleosides", Bioorganic & Medicinal Chemistry Letters 8 (1998) pp. 989-992.
Hua Lin et al., "Highly Efficient Asymmetric Synthesis of Enantiopure Dihydro-1,2-oxazines: Dual-Organocatalyst-Promoted Asymmetric Cascade Reaction", Organic Letters (2012), vol. 14, No. 15; pp. 3818-3821.
Houssine Ait-sir et al., "Synthesis and configurational assignments of 3-substituted 2-deoxy-4-thio-Derythro-pentofuranose derivatives", Journal of the Chemical Society, Perkin transactions 1,1996; No. 14 pp. 1665-1671.
Hayato Fujita et al., "Gene Expression Levels as Predictive Markers of Outcome in Pancreatic Cancer after Gemcitabine-Based Adjuvant Chemotherapyl ,2", Neo Plasia, Oct. 2010, pp. 807-817, vol. 12, No. 10.
Hironobu Hashimoto et al., "Novel conversion of aldopyranosides into 5-thioaldopyranosides via acyclic monothioacetals with inversion and retention of configuration at C-5", Carbohydrate Research, vol. 282, Issue 2 (Feb. 23, 1996) pp. 207-221.
G. Inguaggiato et al., "Novel Triazole 2,-Deoxy - 4 - Thionucleosides: Stereoselective Synthesis and Biological Evaluation", Nucleosides & Nucleotides, 1999; vol. 18, No. 3; pp. 457-467.
Extended European Search Report (EESR) dated Oct. 12, 2015 issued in European patent application No. 13770090.2.
Extended European Search Report dated Mar. 16, 2017 issued in European Patent Application No. 17150141.4.
Extended European Search Report for Application No. 13879640.4 dated May 18, 2016.
Feng Zheng et al., "Synthesis of L-B-3'Deoxy -2',3'-difluoro-4'-thionucleosides", Organic Letters, 2006, pp. 6083-6086, vol. 8, No. 26.
Elmer J. Reist et al., "Synthesis the 4-Thio-D-and-L-Ribofuranose and the Corresponding Adenine Nucleosides", Journal of the American Chemical Society, 1964, 86(24), pp. 5658-5663.
Eva Bozo et al., "Synthesis of 4-cyanophenyl and 4-nitrophenyl 1,5-dithio-L-and -D- arabinopyranosides possessing antithrombotic activity12", Carbohydrate Research 1998, vol. 311; pp. 191-202.
Elmer J. Reist et al., "Thio Sugars, Synthesis of the Adenine Nucleosides of 4-Thio-D-Xylose and 4-Thio-D-Arabinose", Journal of Organic Chemistry, 1968, 33(1) pp. 189-192.
Extended European Search Report (EESR) issued in European application No. 14177042.0 dated Oct. 2, 2014.
Extended European Search Report (EESR) issued in application No. 15853887.6 dated Aug. 17, 2 017.
Deborah A. Zajchowski et al., "Anti-tumor efficacy of the nucleoside analog 1-(-deoxy-2-fluoro-4-thio-B-D-arabinofuranosyl) cytosine (4'-thio-FAC) on human pancreatic and ovarian tumor xenograft models", Int. J. Cancer, 2005, pp. 1002-1009, vol. 114.
Dusan Miljkovic et al., "An improved synthesis of methyl S-thio-D-arabino-pyranosides", Journal of the Serbian Chemical Society, vol. 55, 1990; pp. 359-361.
David A. Berges et al.5 "Bicyclic diazasugars. Part 3: 6-D-Mannose and 6-deoxy-6-L-gulose analogues", Tetrahedron, 2001, vol. 57; pp. 9915-9924.

(56) References Cited

OTHER PUBLICATIONS

Cottrell et al. "Reactions of Sugar Chlorosulfates", Canadian Journal of Chemistry, Jul. 1, 1966, vol. 44, No. 13, pp. 1483-1491 (9 pages total).
Cox, J.M., et al., "Cyclic Hemithioacetals: Analogues of Thiosugars with Sulphur in the Ring", J. Chern. Soc., Section C, 1967, pp. 1130-1134.
Communication dated Sep. 12, 2016 from the U.S. Patent and Trademark Office in U.S. Appl. No. 14/873,966.
Communication dated Nov. 30, 2015 from the U.S. Patent and Trademark Office in U.S. Appl. No. 14/621,119.
Communication dated May 8, 2017, from the European Patent Office in European application No. 13879640.4.
Corrected Notice of Allowability dated Nov. 17, 2017 from the United States Patent and Trademark Office in U.S. Appl. No. 14/498,334.
Communication dated May 19, 2017, issued from the Europe Patent Office in European Patent Application No. 13770090.2.
Communication dated Mar. 28, 2017 from the European Patent Office in European Application No. 15751531.3.
Office Action dated Mar. 22, 2018, issued by the Korean Intellectual Property Office in Korean Application No. 10-2017-70183372.
Office Action dated Mar. 27, 2018 from the Intellectual Property Office of India in Application No. 1391/CHENP/2015.
Communication dated Jun. 14, 2017 from the State of Israel Patent Office in application No. 237086.
Communication dated Mar. 13, 2017 from the U.S. Patent and Trademark Office in U.S. Appl. No. 15/238,232.
Communication dated Jan. 31, 2 017 from the European Patent Office in application No. 15751503.2.
Communication dated Jul. 2, 2015 from the U.S. Patent and Trademark Office in U.S. Appl. No. 14/621,119.
Communication dated Apr. 4, 2017 from the Japanese Patent Office in Japanese Application No. 2014029978.
Communication dated Jan. 23, 2018 from the Japanese Patent Office in application No. 2016-556227.
Office Action dated Apr. 12, 2018 from the Canadian Patent Office in Canadian application No. 2966138.
Communication dated Apr. 18, 2017 from the Japanese Patent Office in application No. 2016-504110.
Office Action dated Apr. 28, 2018 from the Russian Patent Office in Russian application No. 2017114338/04.
Communication dated Apr. 26, 2017, issued from the Mexico Patent Office in Mexican Patent Application No. MX/a/2014/011182.
Attardo, G., et al., "Efficient Synthesis of 5,8-Disubstituted-1,4-Dihydrobenzoxathiin-3-Oxides and Their Isomeric Structures, 4,7-Disubstituted-1,3-Dihydrobenzo[b] Thiophene-2,2-Dioxides", Tetrahedron Letters, vol. 35, No. 27, 1994, pp. 4743-4746 (4 pages).
Australian Office Action of Application No. 213303534 dated Dec. 1, 2015.
Chia-Lin J. Wang et al., "Synthesis of 2'(S), 3'(R), 5'-Trihydroxypentyladenine", Tetrahedron letters, 1988, pp. 1107-1110, vol. 29, No. 10.
Chinese Office Action for Application No. 201380042642.1, dated Nov. 2, 2015.
Abu T.M. Serajuddin, "Salt formation to improve drug solubility", Advanced Drug Delivery Reviews, 2007, pp. 603-616, vol. 59, No. 7.
Office Action dated Mar. 13, 2017, which issued during the prosecution of U.S. Appl. No. 15/238,784.
Office Action dated May 12, 1999, which issued during the prosecution of U.S. Appl. No. 08/973,529.
Gura et al., Systems for identifying new drugs are often faulty, Science, 278:1041-1042, 1997.
Johnson et al., Relationships between drug activity in NCI preclinical in vitro and in vivo models and early clinical trials, British Journal of Cancer, 84(10): 1424-1431,2001.
Pearce et al., Failure modes in anticancer drug discovery and development, Cancer Drug Design and Discovery, Edited by Stephen Neidle, Chapter 18, pp. 424-435 (2008).
Simone, Oncology; Introduction, Cecil Textbook of Medicine, 20th Edition, vol. 1, pp. 1004-1010, 1995.
International Search Report, issued by International Searching Authority dated May 19, 2015, in International Application No. PCT/JP2015/054305.
International Preliminary Report on Patentability issued from the International Bureau in International Application No. PCT/JP2015/054305, dated Jan. 4, 2016.
International Search Report, issued by International Searching Authority in International Application No. PGT/JP2015/052304, dated Mar. 10, 2015.
H. Driguez et al., "A Novel Synthesis of S-Thio-D-Glucose", Tetrahedron Letters, 1981, vol. 22, No. 50, pp. 5061-5062.
International Preliminary Report on Patentability issued from the International Bureau in International Application No. PCT/JP2015/052304, dated Feb. 16, 2016.
David Baker et al., "Large-scale preparation of D-allose: observations on the stereoselectivity of the Yeduction of 1,2:5,6-di-0-isopropylidene-a-D-ribo-hexofuranos-3-ulose hydrate", Carbohydrate Research, 1972, pp. 192-197, vol. 24.
Office Action dated May 19, 2017, issued from the Canadian Patent Office in Canadian Patent Application No. 2,880,794.
Office Action dated Oct. 27, 2017, from Intellectual Property India in Indian Patent Application No. 6251/CHENP/2012.
Office Action dated Sep. 26, 2017 from the Japanese Patent Office in Japanese Application No. 2016-136575.
Communication dated Sep. 3, 2018 from the Korean Intellectual Property Office in application No. 10-2016-7036051.
Communication dated Sep. 20, 2018 from the Korean Intellectual Property Office in application No. 10-2017-7018337.
Communication dated Jul. 3, 2018, issued by the European Patent Office in European Patent Application No. 17150141.4; 3 pages.
Communication dated May 30, 2018 issued by the Intellectual Property Office of Indonesia in Application No. W00201202819; 4 pages.
Journal of Medical Chemistry, Jan. 28, 2014, vol. 57, No. 4, Abstract (total 1 page).
Communication dated Jan. 29, 2019 from the Intellectual Property India in Indian Application No. 201747015114.
Feng Zheng et al., "Synthesis of L-(3-3'-Deoxy-3', 3'-difluoro-4'-thionucleosides", Organic Letters, vol. 8, No. 26, pp. 6083-6086, 2006, 4 pages total.
Office Action dated Apr. 17, 2019, issued by the State Intellectual Property Office of People's Republic of China in Chinese Application No. 16045047.8, corresponding to subject-matter related U.S. Appl. No. 16/045,047.
Communication dated Mar. 5, 2019 from the Taiwanese Patent Office in TW Application No. 104135717.
Communication dated Jun. 20, 2019, issued by the Mexican Patent Office in Mexican Application No. MX/a/2017/008865.
Office Action dated Sep. 15, 2020 in New Zealand Application No. 751051.
International Preliminary Report on Patentability dated Sep. 15, 2020 in International Application No. PCT/JP2019/010169.
Office Action dated Nov. 5, 2020 in U.S. Appl. No. 16/286,930.
Office Action dated Apr. 13, 2021 from the New Zealand Intellectual Property Office in subject matter-related NZ Application No. 751051.
Communication dated Jul. 13, 2021 issued by the Japan Patent Office in Japanese Patent Application No. 2020-506583.
Office Action dated May 31, 2021 issued by the Taiwanese Patent Office in Taiwanese Application No. 106129543 (corresponding to U.S. Appl. No. 16/286,930).
Office Action dated Jun. 6, 2021 in Israel Application No. 265044, 11 pages, corresponding to subject-matter related U.S. Appl. No. 16/286,930.

* cited by examiner

[Fig. 1]
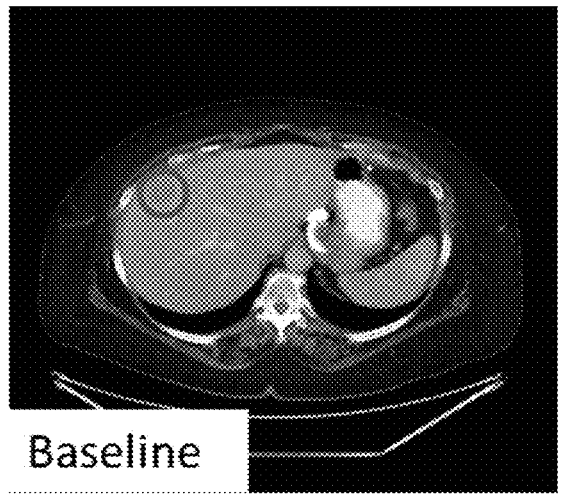
Baseline
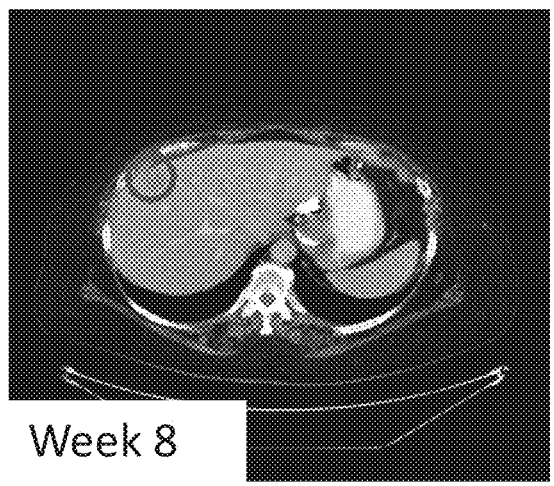
Week 8
Week 16

[Fig. 2]
 

[Fig. 3]
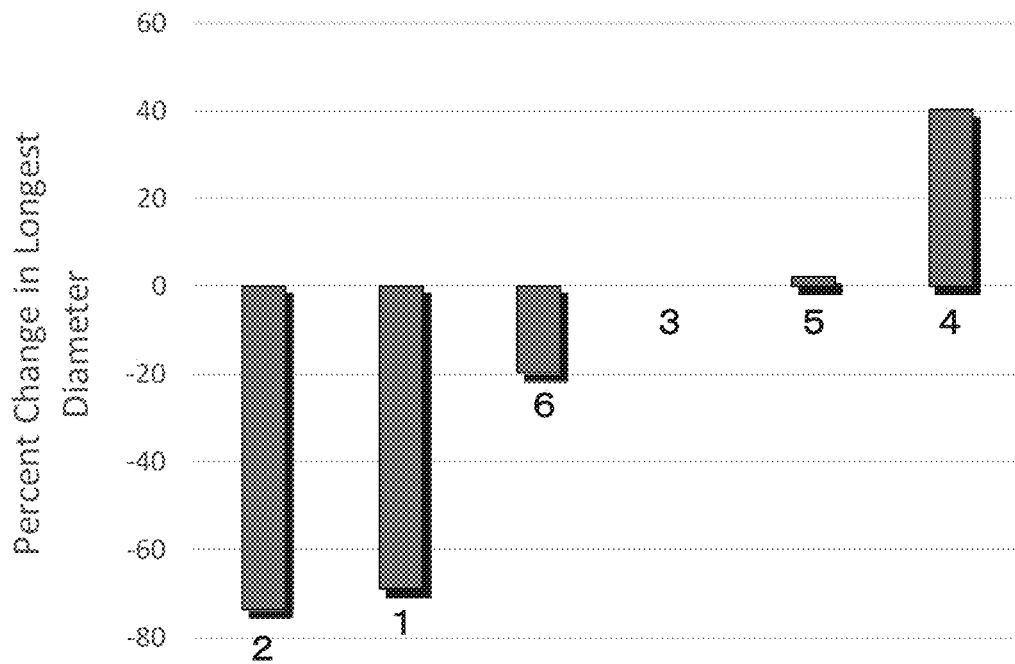
[Fig. 4]
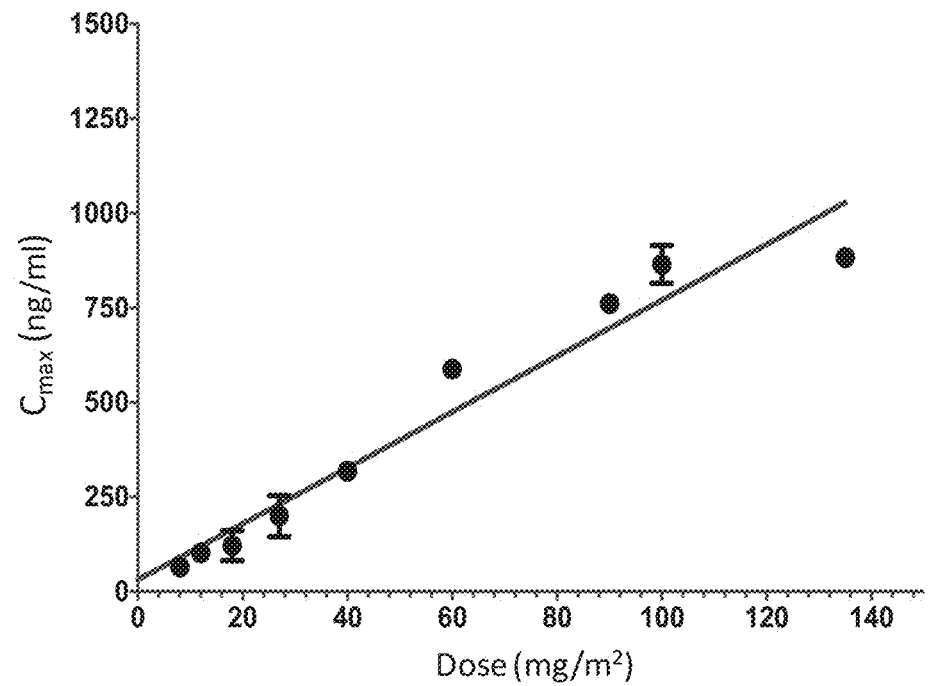

ANTITUMOR AGENT FOR BILIARY TRACT CANCER AND METHOD FOR TREATING BILIARY TRACT CANCER

CROSS-REFERENCE TO RELATED APPLICATIONS

This application is a Continuation of PCT International Application No. PCT/JP2018/007772 filed on Mar. 1, 2018, which claims priority under 35 U.S.C § 119(a) to U.S. Provisional Patent Application No. 62/623,262 filed on Jan. 29, 2018. Each of the above application(s) is hereby expressly incorporated by reference, in its entirety, into the present application.

TECHNICAL FIELD

The present invention relates to an antitumor agent for biliary tract cancer and a method for treating biliary tract cancer.

BACKGROUND ART

It has been known that 1-(2-deoxy-2-fluoro-4-thio-β-D-arabinofuranosyl)cytosine (hereinafter also referred to as "Compound A") has excellent antitumor activity and is useful as an antitumor agent (Patent Document 1). Moreover, Compound A has been known to have strong antitumor activity, even when it is orally administered to mice (Non-Patent Documents 1 to 3). Furthermore, a salt of Compound A, a prodrug of Compound A, an injection comprising Compound A, and a production method thereof have also been known (Patent Documents 2 to 6).

Biliary tract cancer is an extremely highly invasive cancer generated from bile duct epithelial cells. Since biliary tract cancer has a very few clinical symptoms at the early stage of onset, this cancer is often found at the advanced stage in many cases, and the prognosis thereof is poor. The therapy of biliary tract cancer by surgical resection is only a completely curable treatment, but the recurrence rate is high even by this therapy. Chemotherapy is performed on inoperable cases or recurrence cases, but the therapeutic effects are insufficient in many cases.

PRIOR ART DOCUMENTS

Patent Documents

Patent Document 1: International Publication WO 1997/038001
Patent Document 2: International Publication WO 2013/146833
Patent Document 3: International Publication WO 2011/074484
Patent Document 4: International Publication WO 2014/027658
Patent Document 5: International Publication WO 2016/068341
Patent Document 6: International Publication WO 2017/150511

Non-Patent Documents

Non-Patent Document 1: Cancer Letters, 1998, Vol. 129, pp. 103-110
Non-Patent Document 2: Cancer Letters, 1999, Vol. 144, pp. 177-182
Non-Patent Document 3: Oncology Reports, 2002, Vol. 9, pp. 1319-1322

SUMMARY OF INVENTION

Object to be Solved by the Invention

To date, it has not been reported that Compound A specifically exhibits therapeutic effects on biliary tract cancer. It is an object of the present invention to provide an antitumor agent for biliary tract cancer that exhibits effects on biliary tract cancer, and a method for treating biliary tract cancer.

Means for Solving the Object

As a result of intensive studies directed towards achieving the aforementioned object, the present inventors have found that Compound A exhibits therapeutic effects on biliary tract cancer, thereby completing the present invention.

Specifically, the present invention provides the following.
(1) An antitumor agent for biliary tract cancer, comprising 1-(2-deoxy-2-fluoro-4-thio-β-D-arabinofuranosyl)cytosine, a salt thereof, or a prodrug thereof.
(2) The antitumor agent according to the above (1), wherein the biliary tract cancer is bile duct cancer.
(3) The antitumor agent according to the above (1) or (2), wherein the bile duct cancer is extrahepatic bile duct cancer or intrahepatic bile duct cancer.
(4) The antitumor agent according to any one of the above (1) to (3), wherein a single dose is 20 mg/m$^2$ or more, and a course consisting of administration once a week for 3 weeks and the subsequent cessation of medication for 1 week is repeated several times.
(5) The antitumor agent according to the above (4), wherein a single dose is 40 mg/m$^2$ to 200 mg/m$^2$.
(6) The antitumor agent according to the above (4), wherein a single dose is 80 mg/m$^2$ to 150 mg/m$^2$.
(7) The antitumor agent according to any one of the above (1) to (6), which is an injection.
(8) A method for treating biliary tract cancer, comprising administering a therapeutically effective amount of 1-(2-deoxy-2-fluoro-4-thio-β-D-arabinofuranosyl)cytosine, a salt thereof, or a prodrug thereof to a subject (a mammal including a human), or
a method of administering an antitumor agent to a patient suffering from biliary tract cancer, wherein the antitumor agent comprises 1-(2-deoxy-2-fluoro-4-thio-β-D-arabinofuranosyl)cytosine, a salt thereof, or a prodrug thereof.
(9) The method according to the above (8), wherein the biliary tract cancer is bile duct cancer.
(10) The method according to the above (8) or (9), wherein the bile duct cancer is extrahepatic bile duct cancer or intrahepatic bile duct cancer.
(11) The method according to any one of the above (8) to (10), wherein a single dose is 20 mg/m$^2$ or more, and a course consisting of administration once a week for 3 weeks and the subsequent cessation of medication for 1 week is repeated several times.
(12) The method according to the above (11), wherein a single dose is 40 mg/m$^2$ to 200 mg/m$^2$.
(13) The method according to the above (11), wherein a single dose is 80 mg/m$^2$ to 150 mg/m$^2$.
(14) The method according to any one of the above (8) to (13), wherein the antitumor agent is an injection.
(A) A method of using 1-(2-deoxy-2-fluoro-4-thio-β-D-arabinofuranosyl)cytosine, a salt thereof, or a prodrug thereof for treating biliary tract cancer, wherein the method comprises administering a therapeutically effective amount thereof to a subject (a mammal including a human) in need of such treatment.

(B) A method for treating biliary tract cancer, comprising administering a therapeutically effective amount of 1-(2-deoxy-2-fluoro-4-thio-β-D-arabinofuranosyl)cytosine, a salt thereof, or a prodrug thereof to a subject.

(C) Use of 1-(2-deoxy-2-fluoro-4-thio-β-D-arabinofuranosyl)cytosine, a salt thereof, or a prodrug thereof for the production of an antitumor agent for biliary tract cancer.

(D) 1-(2-Deoxy-2-fluoro-4-thio-β-D-arabinofuranosyl)cytosine, a salt thereof, or a prodrug thereof, for use in the therapy of biliary tract cancer.

Advantageous Effects of Invention

Compound A exhibits therapeutic effects on biliary tract cancer. That is to say, according to the present invention, provided is an antitumor agent for biliary tract cancer that exhibits effects on biliary tract cancer, and a method for treating biliary tract cancer.

BRIEF DESCRIPTION OF DRAWINGS

FIG. 1 shows the results of image diagnosis performed on bile duct cancer patient 1.

FIG. 2 shows the results of image diagnosis performed on bile duct cancer patient 2.

FIG. 3 is a graph which shows the change of long diameter of tumor to Baseline in bile duct cancer patients 1-6.

FIG. 4 is a graph which shows Cmax values of plasma concentration of Compound A in patients to whom Compound A was administered in the clinical trial.

EMBODIMENT OF CARRYING OUT THE INVENTION

In the present invention, the range indicated with the term "to" includes the values at both ends, unless otherwise specified.

The term "subject" is used herein to mean a mammal such as a human, a mouse, a monkey or a livestock animal, which is in need of prevention or therapy, and the subject is preferably a human in need of prevention or therapy.

The term "prevention" is used herein to mean inhibition of the onset, reduction of an onset risk, retardation of the onset, etc.

The term "therapy" is used herein to mean amelioration of the target disease or condition, suppression of the progression (maintenance or retardation), etc.

The term "treating" is used herein to mean prevention, therapy and the like, which are performed on various types of diseases.

The term "tumor" is used herein to mean a benign tumor or a malignant tumor. The term "benign tumor" is used herein to mean a tumor having neither invasive property nor metastasis, in which tumor cells and the sequences thereof are close to those of the normal cells as origins.

The term "malignant tumor" is used herein to mean a tumor having invasive property or metastasis, in which tumor cells and the sequences thereof are different from those of the normal cells as origins.

Hereafter, the present invention will be described in detail.

The present invention relates to an antitumor agent for biliary tract cancer, comprising 1-(2-deoxy-2-fluoro-4-thio-β-D-arabinofuranosyl)cytosine (Compound A), a salt thereof, or a prodrug thereof.

Compound A, Salt Thereof, or Prodrug Thereof

First, Compound A, a salt thereof, or a prodrug thereof will be described.

The salt used herein is a pharmaceutically acceptable salt. Specific examples of the salt include mineral acid salt, organic carboxylate, and sulfonate. Preferred salts include mineral acid salt and sulfonate.

Examples of the mineral acid salt include hydrochloride, hydrobromide, hydroiodide, nitrate, phosphate, and sulfate. Among these, hydrochloride, hydroiodide, nitrate or sulfate is preferable, and hydrochloride is more preferable. Examples of the organic carboxylate include formate, acetate, citrate, oxalate, fumarate, maleate, succinate, malate, tartrate, aspartate, trichloroacetate, and trifluoroacetate. Examples of the sulfonate include methanesulfonate, benzenesulfonate, p-toluenesulfonate, mesitylenesulfonate, and naphthalenesulfonate. Among these, methanesulfonate is preferable.

The salt of Compound A may be any one of an anhydride, a hydrate and a solvate. When the term "salt" is simply used in the present description, the form of the salt may be an anhydride, a hydrate, or a solvate. When the term "anhydride" is used in the present description, it means a case where the salt is neither a hydrate nor a solvate, unless otherwise specified. The salt of Compound A, which does not have crystallization water, hydration water and a solvent interacting therewith, although it is a substance that does not originally form a hydrate or a solvate, is included in the "anhydride" of the present invention. The anhydride may also be referred to as an "anhydrate." When the salt of Compound A is a hydrate, the number of hydration water is not particularly limited, and it can be a monohydrate, a dihydrate and the like. Examples of the solvate include a methanol solvate, an ethanol solvate, a propanol solvate, and a 2-propanol solvate.

Specific examples of the particularly preferred salt of Compound A are the following:
methanesulfonate of 1-(2-deoxy-2-fluoro-4-thio-β-D-arabinofuranosyl)cytosine;
hydrochloride of 1-(2-deoxy-2-fluoro-4-thio-β-D-arabinofuranosyl)cytosine; and
an anhydride of any one of the above-described salts.

The prodrug means a compound whose functional group functioning as a prodrug is cleaved by reaction with intracorporal enzyme, gastric juice, etc., after administration, and is converted to a compound exhibiting pharmacological activity of interest, or a salt thereof.

Examples of a group that forms a prodrug include the groups described in Stella V J et al., Prodrugs: Challenges and Rewards. Parts 1 and 2, 2007, American Association of Pharmaceutical Scientists.

The prodrug of Compound A means a compound, which is converted to Compound A or a phosphoric acid compound thereof by reaction with enzyme, gastric juice, etc., in vivo under physiological conditions, or a salt thereof.

For the prodrug of Compound A, the description of International Publication WO 2016/068341 can be referenced and considered, and thus, the content of International Publication WO 2016/068341 is incorporated into the present description.

More specifically, for example, the thionucleoside derivative represented by the formula [1] described in International Publication WO 2016/068341, or a salt thereof, is incorporated into the present description, and the preferred range is also identical to that described in International Publication WO 2016/068341.

In the present invention, Compound A, a salt thereof, or a prodrug thereof may be used alone, or may also be used in combination of two or more types.

Next, a method for producing Compound A, a salt thereof, or a prodrug thereof will be described. Compound A can be produced, for example, by the methods described in Patent Document 1 and Journal of Organic Chemistry, 1999, Vol. 64, pp. 7912-7920. The salt, hydrate, or solvate of Compound A can be produced, for example, by the method described in Patent Document 4. The prodrug of Compound A can be produced, for example, by the method described in International Publication WO 2016/068341.

Compound A, a salt thereof, or a prodrug thereof according to the present invention can be used as an antitumor agent, or as an active ingredient for pharmaceutical compositions.

Antitumor Agent for Biliary Tract Cancer

According to the present invention, an antitumor agent for biliary tract cancer, which comprises 1-(2-deoxy-2-fluoro-4-thio-β-D-arabinofuranosyl)cytosine, a salt thereof, or a prodrug thereof, is provided.

The biliary tract cancer is preferably bile duct cancer, and more preferably extrahepatic bile duct cancer or intrahepatic bile duct cancer.

In general, the antitumor agent of the present invention may comprise additives such as an emulsifier, a surfactant, a solubilizer, a suspending agent, a tonicity agent, a buffer, an antiseptic, an antioxidant, a stabilizer, and an absorption promoter.

The administration routes of the antitumor agent of the present invention include methods involving an intravenous, intra-arterial, intrarectal, introperitoneal, intramuscular, intratumoral or intravesical injection, and methods such as oral administration, percutaneous administration, and/or use of a suppository. The administration methods include administration involving syringe or intravenous drip.

With regard to the applied dose of Compound A, a salt thereof or a prodrug thereof, and the number of administrations, it can be administered at a dose of 1 to 2000 mg/m$^2$ per day, once or divided over several administrations. The daily dose is preferably 20 mg/m$^2$ or more, preferably 40 mg/m$^2$ or more, and preferably 60 mg/m$^2$ or more. The upper limit of the daily dose is preferably 200 mg/m$^2$, more preferably 150 mg/m$^2$, further preferably 120 mg/m$^2$, particularly preferably 100 mg/m$^2$. The daily dose is more preferably 40 mg/m$^2$ to 200 mg/m$^2$, further preferably 40 mg/m$^2$ to 150 mg/m$^2$, further preferably 80 mg/m$^2$ to 150 mg/m$^2$, still further preferably 80 mg/m$^2$ to 120 mg/m$^2$. However, the applied dose and the number of administrations are not limited thereto.

With regard to the administration method, a single dose is set at 20 mg/m$^2$ or more, and a course consisting of administration once a week for 3 weeks and the subsequent cessation of medication for 1 week can be repeated several times. In this case, the single dose is the same as the daily dose as mentioned above, and is preferably 40 mg/m$^2$ to 200 mg/m$^2$, more preferably 40 mg/m$^2$ to 150 mg/m$^2$ and further preferably 80 mg/m$^2$ to 150 mg/m$^2$.

An example of the dosage form of the antitumor agent for biliary tract cancer of the present invention is a liquid pharmaceutical preparation, and for example, it is an injection. Such dosage form can be produced by methods for producing preparations that are generally known to persons skilled in the art.

The liquid pharmaceutical preparation preferably comprises Compound A or a salt thereof, polyhydric alcohol having a molecular weight of 100 or less, and water.

The content of Compound A or a salt thereof in the liquid pharmaceutical preparation is preferably 1 to 50 mg/mL, more preferably 5 to 50 mg/mL, and particularly preferably 10 to 30 mg/mL.

The polyhydric alcohol having a molecular weight of 100 or less is preferably polyhydric alcohol containing 3 or 4 carbon atoms, more preferably glycerin, propylene glycol or butanediol, and particularly preferably glycerin. Besides, examples of the butanediol include 1,2-butanediol, 1,3-butanediol, 1,4-butanediol, and 2,3-butanediol. Among these, 1,3-butanediol is particularly preferable. The lower limit of the molecular weight of polyhydric alcohol is not particularly limited, and it is generally 50 or more.

The content of the polyhydric alcohol having a molecular weight of 100 or less in the liquid pharmaceutical preparation is preferably 0.5% to 10% by mass, more preferably 0.5% to 5% by mass, and further preferably 1.0% to 2.5% by mass.

The pH of the liquid pharmaceutical preparation is preferably pH 1.5 to 6.9, more preferably pH 1.5 to 6.5, even more preferably pH 2.0 to 6.5, further preferably pH 2.0 to 5.0, still further preferably pH 2.0 to 4.0, particularly preferably pH 2.6 to 3.2, and most preferably pH 2.8 to 3.0.

For the liquid pharmaceutical preparation, the description of International Publication WO 2017/150511 can be referenced and considered, and thus, the content of International Publication WO 2017/150511 is incorporated into the present description. Moreover, the preferred composition and the preferred mixing ratio of the liquid pharmaceutical preparation are also identical to those described in International Publication WO 2017/150511.

The antitumor agent for biliary tract cancer of the present invention can be effectively used for treating biliary tract cancer. The antitumor agent for biliary tract cancer of the present invention can be used as an anticancer agent.

The present invention provides a method of administering an antitumor agent to a patient suffering from biliary tract cancer, wherein the antitumor agent comprises 1-(2-deoxy-2-fluoro-4-thio-β-D-arabinofuranosyl)cytosine, a salt thereof, or a prodrug thereof.

The present invention provides a method of using 1-(2-deoxy-2-fluoro-4-thio-β-D-arabinofuranosyl)cytosine, a salt thereof, or a prodrug thereof for treating biliary tract cancer, wherein the method comprises administering a therapeutically effective amount thereof to a subject (a mammal including a human) in need of such treatment.

The subject may be a patient to whom gemcitabine has been administered as a pre-treatment.

The subject may be a patient to whom gemcitabine has been administered as a pre-treatment, and who could not obtain more effects than Partial Response.

The subject may be a patient on whom a combination chemotherapy including gemcitabine has been performed as a pre-treatment.

The subject may be a patient on whom a combination chemotherapy including gemcitabine has been performed as a pre-treatment, and who could not obtain more effects than Partial Response.

The subject may be a patient on whom other chemotherapy has been performed.

The subject may be a patient who cannot expect to be ameliorated by other chemotherapy.

According to the present invention, the above-described patient who has not conventionally expected to obtain therapeutic effects can obtain amelioration effects.

The present invention provides a method for treating biliary tract cancer, comprising administering a therapeutically effective amount of 1-(2-deoxy-2-fluoro-4-thio-β-D-arabinofuranosyl)cytosine, a salt thereof, or a prodrug thereof to a subject.

The present invention provides use of 1-(2-deoxy-2-fluoro-4-thio-β-D-arabinofuranosyl)cytosine, a salt thereof, or a prodrug thereof for the production of an antitumor agent for biliary tract cancer.

The present invention provides 1-(2-deoxy-2-fluoro-4-thio-β-D-arabinofuranosyl)cytosine, a salt thereof, or a prodrug thereof, for use in the therapy of biliary tract cancer.

EXAMPLES

Hereinafter, the present invention will be described in more detail in the following examples. However, these examples are not intended to limit the scope of the present invention.

Example 1

Preparation of Methanesulfonate of Compound A

Methanesulfonate of 1-(2-deoxy-2-fluoro-4-thio-β-D-arabinofuranosyl)cytosine (hereinafter also referred to as "Compound A") was synthesized in accordance with the method described in International Publication WO 2013/146833 (see Example 22 described in paragraph 0487 to paragraph 0492), and it was used in the subsequent test.

Preparation of Liquid Pharmaceutical Composition

The methanesulfonate of Compound A was dissolved in a suitable amount of water for injection, and the pH of the solution was then adjusted using a 1 mol/L sodium hydroxide aqueous solution. A suitable amount of water for injection was added to and mixed with the above-prepared solution, so that the concentration of Compound A became 20 mg/mL.

Thereafter, glycerin (manufactured by Merck, molecular weight: 92) was added to the above-mixed solution to a concentration of 1.5% by mass. The pH of this liquid pharmaceutical preparation was pH 2.9. This liquid was filtrated through a membrane filter (0.22 μm) to obtain a liquid pharmaceutical preparation.

This liquid pharmaceutical preparation was used in the subsequent therapy. Besides, the therapy was carried out at the University of Texas MD Anderson Cancer Center (hereinafter referred to as MDACC), and at Sarah Cannon Research Institute (hereinafter referred to as SCRI) in Denver, State of Colorado, U.S.A.

Administration and Judgement of Therapeutic Effects

A medication cycle consisting of administration of Compound A via intravenous injection once a week from the $1^{st}$ week to the $3^{rd}$ week and cessation of medication in the $4^{th}$ week was repeated to bile duct cancer patients Specifically, 28 days was set at one cycle, and on the $1^{st}$ day, $8^{th}$ day and $15^{th}$ day, Compound A was administered to the patients. This cycle consisting of 28 days was repeated. A single dose of compound A was set from 40 $mg/m^2$ to 135 $mg/m^2$.

The therapeutic effects were judged according to the following criteria.

Evaluation targets were confirmed by performing image diagnosis using MRI (magnetic resonance imaging), and were then judged according to the following criteria:

CR (Complete Response): A state in which the tumor completely disappeared.

PR (Partial Response): A state in which a sum of the sizes of the tumors was reduced by 30% or more.

SD (Stable Disease): A state in which the size of the tumor did not change.

PD (Progressive Disease): A state in which a sum of the sizes of the tumors was increased by 20% or more and also, the size was increased by 5 mm or more even at an absolute value, or a new lesion appeared.

Bile Duct Cancer Patient 1

Compound A was administered to a patient with bile duct cancer (intrahepatic bile duct cancer) at a single dose of 40 $mg/m^2$. After completion of 4 cycles (16 weeks), 31% of tumor-reducing effect was confirmed in this patient (FIG. 1). This patient had undergone a combination chemotherapy with gemcitabine and cisplatin as a pre-treatment. PR was confirmed even when the single dose was increased to 60 $mg/m^2$ or 90 $mg/m^2$. The results of the pre-treatment were found to be PD. The age and sex of the patient, therapy facility, single dose, therapy history, the therapeutic effects of the present invention, and the like are shown in Table 1, and so forth on.

Bile Duct Cancer Patient 2

Compound A was administered to a patient with bile duct cancer (intrahepatic bile duct cancer) at a single dose of 60 $mg/m^2$. In this patient, after completion of 2 cycles, 31% of tumor-reducing effect was confirmed, and after completion of 4 cycles, 41% of tumor-reducing effect was confirmed (FIG. 2). This patient had undergone a combination chemotherapy with gemcitabine and cisplatin and a combination chemotherapy with gemcitabine and capecitabine as pre-treatments. The results of the pre-treatments were found to be SD. The details are shown in Table 1.

Bile Duct Cancer Patient 3

Bile duct cancer patient 3 is bile duct cholangiocarcinoma. The initial dose was 60 $mg/m^2$, and the dose was changed to 90 $mg/m^2$. SD could be maintained for 32 weeks or more.

Bile Duct Cancer Patient 6

Bile duct cancer patient 6 is intrahepatic cholangiocarcinoma. The initial dose was 135 $mg/m^2$, and the dose was changed to 90 $mg/m^2$ since side effects such as hypotension and suspected bacteremia were observed. Further, due to neutropenia, the dose was changed to 67.5 $mg/m^2$. Thereafter, SD could be maintained for 34 weeks or more.

Bile Duct Cancer Patients 1 to 6

The age and gender of bile duct cancer patients 1 to 6, therapy facility, single dose, pre-therapy (therapy history), ECOG, the therapeutic effects of the present invention, and the like are shown in Table 1.

TABLE 1

| | Age | Gender | Therapy facility | ECOG | Single dose | Therapy history | Therapeutic effects of Gem-Cis | Therapeutic effects of the present invention |
|---|---|---|---|---|---|---|---|---|
| Bile duct cancer patient 1 | 60 | FEMALE | MDACC | 0 | 40 mg/m² | FOLFIRI, IDH305 IDH1 inibitor, Gem-Cis, AG120 IDH1inhibitor | PD | PR 31% reduction by Cycle 4 and remains on study at Cycle 6. |
| Bile duct cancer patient 2 | 68 | FEMALE | SCRI | 1 | 60 mg/m² | FOLFOX, Gem-Cis, Gem-Capecitabine | SD | PR 31% reduction after 2 cycles and 41% reduction after 4 cycles. |
| Bile duct cancer patient 3 | 61 | FEMALE | MDACC | 1 | 60 mg/m² | Gem-Cis | PD | SD |
| Bile duct cancer patient 4 | 57 | MALE | MDACC | 1 | 90 mg/m² | Gem-Cis | SD | PD |
| Bile duct cancer patient 5 | 44 | FEMALE | MDACC | 1 | 90 mg/m² | Gem-Cis | PD | SD |
| Bile duct cancer patient 6 | 57 | FEMALE | SCRI | 1 | 90 mg/m² | Gem-Cis | SD | SD |

In the above table, the term "ECOG" indicates Eastern Cooperative Oncology Groups, the term "Gem-Cis" indicates a combination chemotherapy of using gemcitabine and cisplatin, and the term "Gem-Capecitabine" indicates a combination chemotherapy of using gemcitabine and capecitabine. In addition, in the case of bile duct cancer patients 1 to 2, a plurality of pre-therapies (therapy history) had been carried out. Thus, such history is also shown in the table. ECOG of bile duct cancer patient 1 was 0, and ECOG of bile duct cancer patients 2-6 was 1.

The change of long diameter of tumor to Baseline in bile duct cancer patients 1-6 was showed as a graph (FIG. 3).

Cmax values of plasma concentration of Compound A in 38 patients to whom Compound A was administered in the clinical trial including bile duct cancer patients were showed as a graph (FIG. 4). In the clinical trial, fever, nausea, chills, itch, irritating, dry skin, skin separation, and fatigue were observed as the most common drug associated AE among two or more patients.

INDUSTRIAL APPLICABILITY

The antitumor agent of the present invention is useful as an antitumor agent exhibiting therapeutic effects on biliary tract cancer.

The invention claimed is:

1. A method for treating biliary tract cancer, comprising administering a therapeutically effective amount of 1-(2-deoxy-2-fluoro-4-thio-β-D-arabinofuranosyl)cytosine or a salt thereof to a subject.

2. The method according to claim 1, wherein the biliary tract cancer is bile duct cancer.

3. The method according to claim 1, wherein the bile duct cancer is extrahepatic bile duct cancer or intrahepatic bile duct cancer.

4. The method according to claim 1, wherein a single dose is 20 mg/m² or more, and a course consisting of administration once a week for 3 weeks and the subsequent cessation of medication for 1 week is repeated several times.

5. The method according to claim 4, wherein a single dose is 40 mg/m² to 200 mg/m².

6. The method according to claim 4, wherein a single dose is 80 mg/m² to 150 mg/m².

7. The method according to claim 1, wherein the 1-(2-deoxy-2-fluoro-4-thio-β-D-arabinofuranosyl)cytosine or a salt thereof is an injection.

* * * * *